United States Patent
Kearns et al.

(10) Patent No.: US 9,649,472 B2
(45) Date of Patent: May 16, 2017

(54) MEDICAL PRODUCT PACKAGE

(71) Applicant: Hollister Incorporated, Libertyville, IL (US)

(72) Inventors: Barbara J. Kearns, Balla (IE); Adam J. Foley, Swords (IE); David L. Doerschner, Cary, IL (US); Robert A. Greynolds, Northbrook, IL (US); Jerome A. Henry, Castlebar (IE); Thomas Renehan, Ballina (IE); Horacio Montes De Oca Balderas, Ballina (IE); Shane O'Malley, Ballina (IE); Martin McMenamin, Lifford (IE); Michael G. Murray, Ballina (IE); Brendan J. Heneghan, Westport (IE)

(73) Assignee: Hollister, Inc., Libertyville, IL (US)

( * ) Notice: Subject to any disclaimer, the term of this patent is extended or adjusted under 35 U.S.C. 154(b) by 0 days.

(21) Appl. No.: 14/775,258

(22) PCT Filed: Mar. 14, 2013

(86) PCT No.: PCT/US2013/031480
§ 371 (c)(1),
(2) Date: Sep. 11, 2015

(87) PCT Pub. No.: WO2014/142895
PCT Pub. Date: Sep. 18, 2014

(65) Prior Publication Data
US 2016/0038713 A1  Feb. 11, 2016

(51) Int. Cl.
A61M 25/00 (2006.01)
A61M 25/01 (2006.01)

(52) U.S. Cl.
CPC ....... A61M 25/002 (2013.01); A61M 25/0111 (2013.01); A61M 2210/1085 (2013.01)

(58) Field of Classification Search
CPC ............ A61M 25/002; A61M 25/0111; A61M 2210/1085; B65D 75/30; B65D 75/58; B65D 75/5805
(Continued)

(56) References Cited

U.S. PATENT DOCUMENTS 3,035,691 A  5/1962  Rasmussen et al.
3,186,625 A  6/1965  Mead et al.
(Continued)

FOREIGN PATENT DOCUMENTS

EP  0465329 A2  1/1992
EP  0782868 A1  1/1996
(Continued)

OTHER PUBLICATIONS

Notification Concerning Transmittal of International Preliminary Report on Patentability, International Preliminary Report and Written Opinion of the ISA for PCT/US2013/031480 dated Sep. 24, 2015.

*Primary Examiner* — Chun Cheung
(74) *Attorney, Agent, or Firm* — Cook Alex Ltd.

(57) ABSTRACT

A catheter and package combination including a package having opposed front and rear panels that are sealed together to define a sealed interior cavity. The package also has top and bottom edges and opposed side edges. The cavity has a first height extending in a direction between the top and bottom edges. The front and rear panels are configured to tear adjacent to one of the side edges in the direction between the top and bottom edges to form an opening in communication with the cavity wherein the opening has a second height in the direction between the top and bottom edges that is smaller than the first height of the cavity. A urinary catheter in a compact configuration is disposed within the cavity.

20 Claims, 6 Drawing Sheets

(58) Field of Classification Search
USPC .................................................. 383/200–209
See application file for complete search history.

(56) References Cited

U.S. PATENT DOCUMENTS

| | | | |
|---|---|---|---|
| 3,485,352 A | 12/1969 | Pilger | |
| 3,642,126 A | 2/1972 | Kurtz et al. | |
| 3,703,174 A | 11/1972 | Smith | |
| 3,750,875 A | 8/1973 | Juster | |
| 3,926,309 A | 12/1975 | Center | |
| 3,934,721 A | 1/1976 | Juster et al. | |
| 4,183,434 A | 1/1980 | Watt | |
| 4,216,860 A | 8/1980 | Heimann | |
| 4,332,327 A | 6/1982 | Frohwerk et al. | |
| 4,685,902 A | 8/1987 | Edwards et al. | |
| 4,721,123 A | 1/1988 | Cosentino et al. | |
| 4,790,829 A | 12/1988 | Bowden et al. | |
| 4,834,245 A | 5/1989 | Ohga et al. | |
| 4,858,821 A | 8/1989 | Bickelhaupt | |
| 4,890,744 A | 1/1990 | Lane, Jr. et al. | |
| 4,903,841 A | 2/1990 | Ohsima et al. | |
| 5,038,547 A | 8/1991 | Kai et al. | |
| 5,129,889 A | 7/1992 | Hahn et al. | |
| 5,163,554 A | 11/1992 | Lampropoulos et al. | |
| 5,322,163 A | 6/1994 | Foos | |
| 5,344,011 A | 9/1994 | DiBernardo et al. | |
| 5,353,985 A | 10/1994 | Nageli et al. | |
| 5,354,132 A | 10/1994 | Young et al. | |
| 5,372,254 A | 12/1994 | Gross | |
| 5,372,589 A | 12/1994 | Davis | |
| 5,447,231 A | 9/1995 | Kastenhofer | |
| 5,470,419 A | 11/1995 | Sasaki et al. | |
| 5,590,778 A | 1/1997 | Dutchik | |
| 5,836,697 A | 11/1998 | Chiesa | |
| 5,848,691 A | 12/1998 | Morris et al. | |
| 5,895,374 A | 4/1999 | Rodsten | |
| 6,053,313 A | 4/2000 | Farrell et al. | |
| 6,059,107 A | 5/2000 | Nosted et al. | |
| 6,062,413 A | 5/2000 | Redmond | |
| 6,065,597 A | 5/2000 | Pettersson et al. | |
| 6,068,121 A | 5/2000 | McGlinch | |
| 6,146,017 A | 11/2000 | Hodges | |
| 6,174,083 B1 | 1/2001 | Delefortrie et al. | |
| 6,228,458 B1 | 5/2001 | Pinchen et al. | |
| 6,299,012 B1 | 10/2001 | Redmond | |
| 6,318,893 B1 | 11/2001 | Gates | |
| 6,354,739 B1* | 3/2002 | Sheehan, Jr. | B65D 75/66 229/123.2 |
| 6,355,004 B1 | 3/2002 | Pedersen et al. | |
| 6,409,717 B1 | 6/2002 | Israelsson et al. | |
| D464,257 S | 10/2002 | Gates | |
| D466,004 S | 11/2002 | Gates | |
| D466,005 S | 11/2002 | Gates | |
| 6,485,177 B2 | 11/2002 | Bell | |
| 6,578,709 B1 | 6/2003 | Kavanagh et al. | |
| 6,634,498 B2 | 10/2003 | Kayerod et al. | |
| 6,702,462 B2 | 3/2004 | Richardson | |
| 6,719,135 B2 | 4/2004 | Armijo | |
| 6,736,805 B2 | 5/2004 | Israelsson et al. | |
| 6,745,545 B2 | 6/2004 | Schneider et al. | |
| 6,848,574 B1 | 2/2005 | Israelsson et al. | |
| 6,902,057 B2 | 6/2005 | Duffy | |
| 6,994,213 B2 | 2/2006 | Giard, Jr. et al. | |
| 7,000,770 B2 | 2/2006 | Clarke et al. | |
| 7,104,399 B2 | 9/2006 | Duffy et al. | |
| 7,234,597 B2 | 6/2007 | Rowe et al. | |
| 7,306,371 B2 | 12/2007 | Perell | |
| 7,331,462 B2 | 2/2008 | Steppe | |
| 7,334,679 B2 | 2/2008 | Givens, Jr. | |
| 7,380,658 B2 | 6/2008 | Murray et al. | |
| 7,434,687 B2 | 10/2008 | Itou et al. | |
| 7,549,276 B2 | 6/2009 | Rowe et al. | |
| 7,631,760 B2 | 12/2009 | Guelzow et al. | |
| 7,743,918 B2 | 6/2010 | Itou et al. | |
| 7,766,162 B2 | 8/2010 | Maki et al. | |
| 7,770,726 B2* | 8/2010 | Murray | A61M 25/0111 206/210 |
| 7,770,728 B2 | 8/2010 | Kaern | |
| 7,789,873 B2 | 9/2010 | Kubalak et al. | |
| 7,886,906 B1 | 2/2011 | Dunn | |
| 8,021,049 B2 | 9/2011 | Smith | |
| 8,051,981 B2 | 11/2011 | Murray et al. | |
| 8,128,595 B2 | 3/2012 | Walker et al. | |
| 8,205,745 B2 | 6/2012 | Murray et al. | |
| 8,235,209 B2 | 8/2012 | Peck et al. | |
| 8,240,468 B2 | 8/2012 | Wilkinson et al. | |
| 8,313,461 B2 | 11/2012 | Walker et al. | |
| 8,662,306 B2 | 3/2014 | Agrawal | |
| D705,925 S | 5/2014 | Murray et al. | |
| 8,870,819 B2 | 10/2014 | Walker et al. | |
| 9,038,822 B2 | 5/2015 | Barnell | |
| 9,044,572 B2 | 6/2015 | Nakamoto et al. | |
| D747,184 S | 1/2016 | Murray et al. | |
| 9,259,349 B2 | 2/2016 | Walker et al. | |
| 2001/0054562 A1* | 12/2001 | Pettersson | B32B 27/08 206/364 |
| 2002/0184857 A1 | 12/2002 | O'Connor et al. | |
| 2004/0153051 A1 | 8/2004 | Israelsson et al. | |
| 2004/0243214 A1 | 12/2004 | Farrell et al. | |
| 2005/0007882 A1 | 1/2005 | Bachelor et al. | |
| 2005/0084636 A1 | 4/2005 | Papenfuss et al. | |
| 2005/0109648 A1 | 5/2005 | Kerzman et al. | |
| 2005/0199521 A1* | 9/2005 | Givens, Jr. | A61M 25/002 206/364 |
| 2007/0177828 A1 | 8/2007 | Takada et al. | |
| 2008/0006554 A1 | 1/2008 | Duffy et al. | |
| 2008/0031555 A1 | 2/2008 | Roberts | |
| 2008/0063324 A1* | 3/2008 | Bernard | B65D 75/5811 383/200 |
| 2008/0179208 A1 | 7/2008 | Murray et al. | |
| 2008/0287798 A1 | 11/2008 | Lee et al. | |
| 2009/0131917 A1 | 5/2009 | Kavanagh et al. | |
| 2009/0161995 A1* | 6/2009 | Henderson | B65D 75/5855 383/210 |
| 2009/0200198 A1 | 8/2009 | Guelzow et al. | |
| 2010/0263327 A1 | 10/2010 | Murray et al. | |
| 2011/0127186 A1 | 6/2011 | Enns et al. | |
| 2011/0284409 A1 | 11/2011 | Murray et al. | |
| 2012/0261290 A1 | 10/2012 | Limjaroen et al. | |
| 2013/0345561 A1 | 12/2013 | Quigley | |
| 2015/0018803 A1 | 1/2015 | Tjassens et al. | |
| 2015/0202405 A1 | 7/2015 | Schertiger et al. | |
| 2015/0335854 A1 | 11/2015 | Dvarsater et al. | |
| 2015/0352316 A1 | 12/2015 | Terzibashian | |
| 2016/0001037 A1 | 1/2016 | Hong et al. | |
| 2016/0038713 A1 | 2/2016 | Kearns et al. | |
| 2016/0082223 A1 | 3/2016 | Barnell | |
| 2016/0136391 A1 | 5/2016 | Foley et al. | |
| 2016/0193444 A1 | 7/2016 | Tomes et al. | |
| 2016/0228676 A1 | 8/2016 | Glithero et al. | |

FOREIGN PATENT DOCUMENTS

| | | |
|---|---|---|
| EP | 0820781 A1 | 7/1997 |
| EP | 0935478 B1 | 1/2000 |
| EP | 0988847 A2 | 3/2000 |
| EP | 0680896 B2 | 9/2000 |
| EP | 0923398 B1 | 11/2001 |
| EP | 1245205 A2 | 10/2002 |
| EP | 0959930 B1 | 12/2002 |
| EP | 1115450 B1 | 11/2004 |
| EP | 1145729 B1 | 11/2005 |
| EP | 1472155 B1 | 4/2007 |
| EP | 2106821 A1 | 3/2008 |
| EP | 1958656 A1 | 8/2008 |
| JP | 10139048 | 5/1998 |
| JP | 2010-139148 A | 6/2010 |
| WO | WO 01/78824 | 10/2001 |
| WO | WO2007/146820 A2 | 12/2007 |
| WO | WO 2015/157462 A1 | 10/2015 |
| WO | WO 2016/069868 A1 | 5/2016 |

* cited by examiner

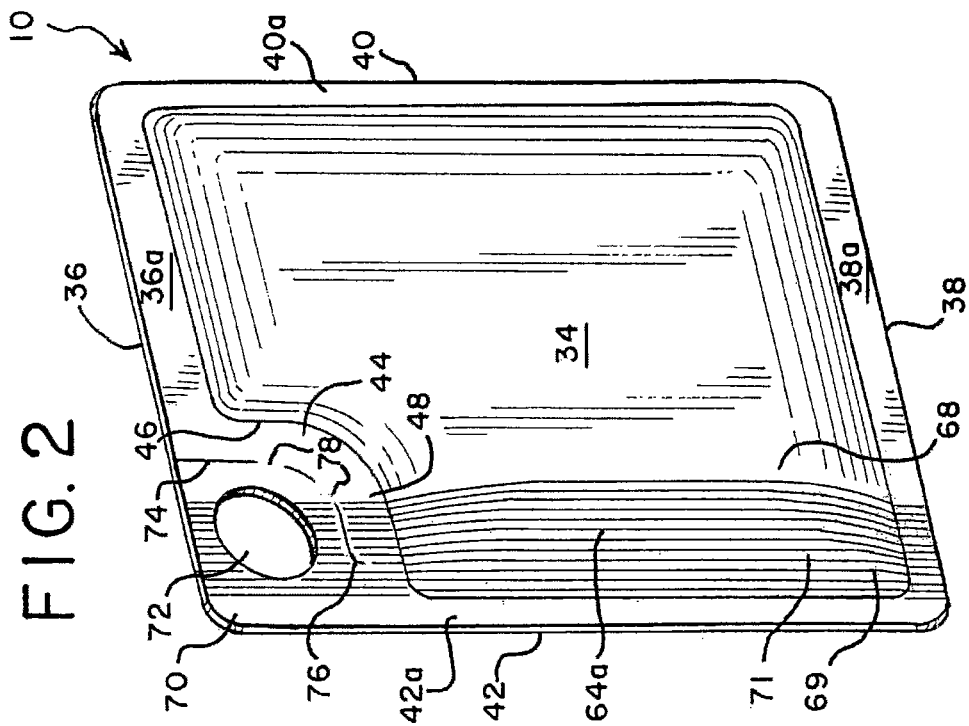
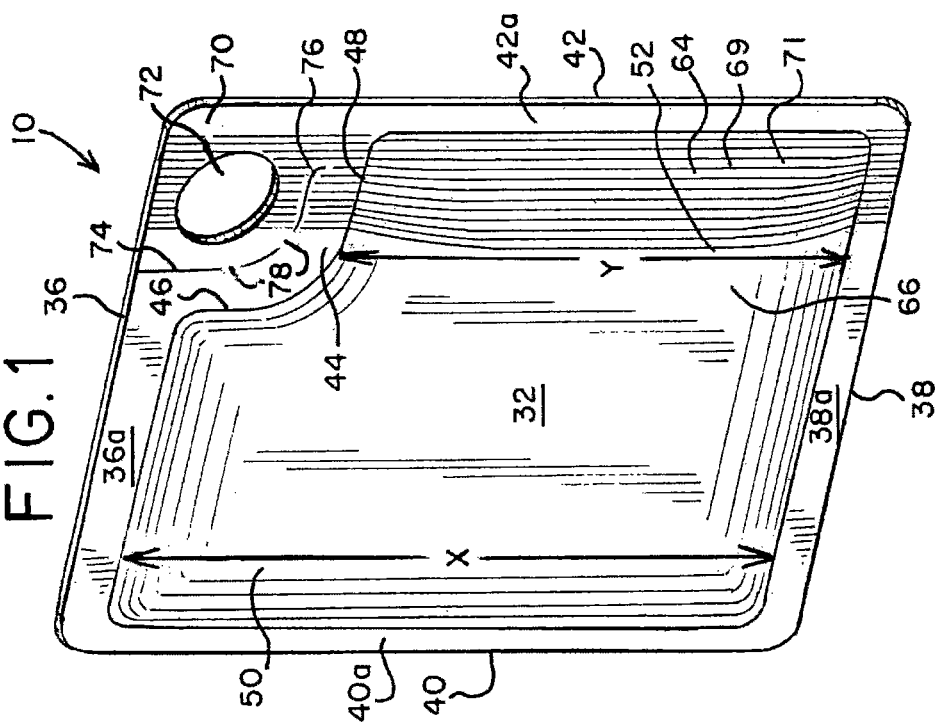

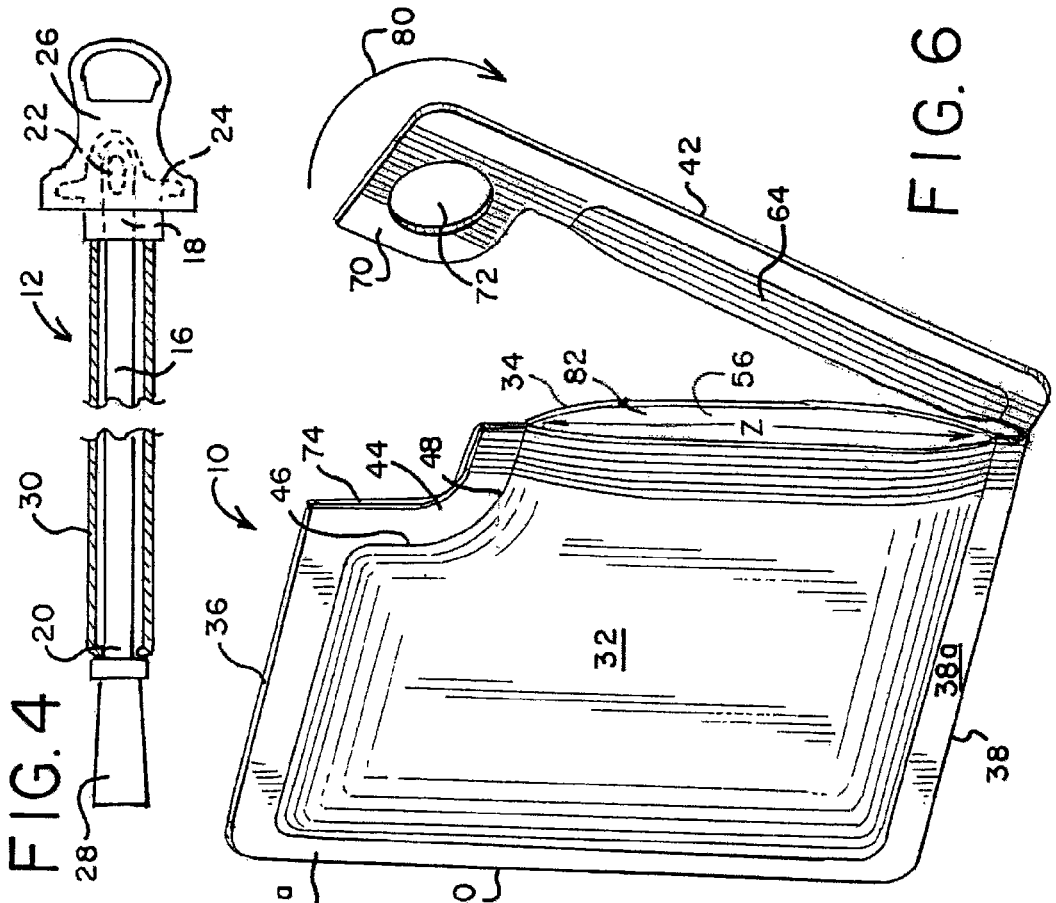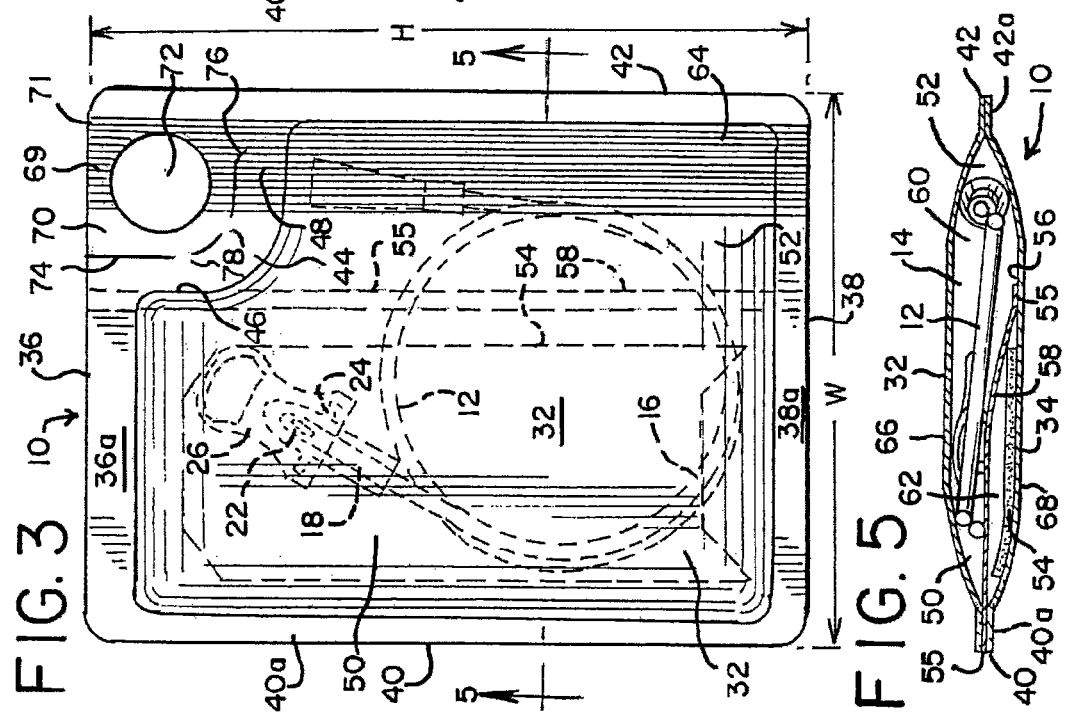

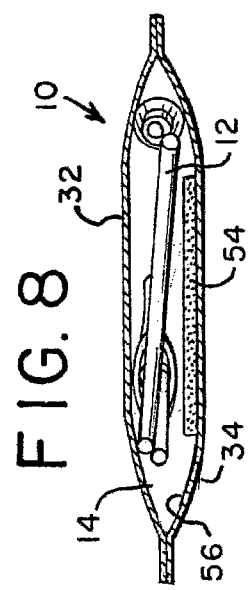
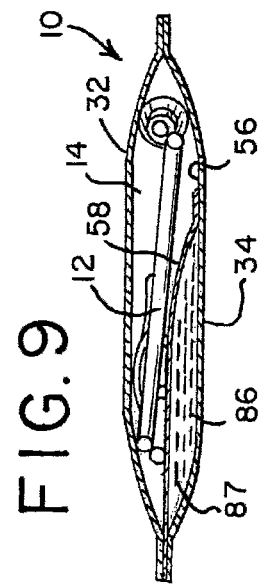
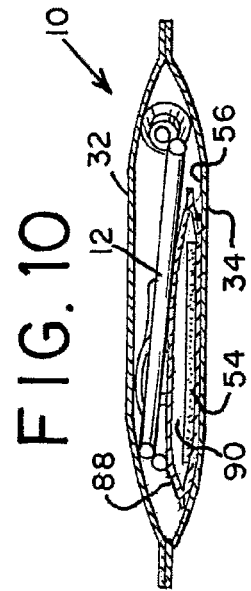
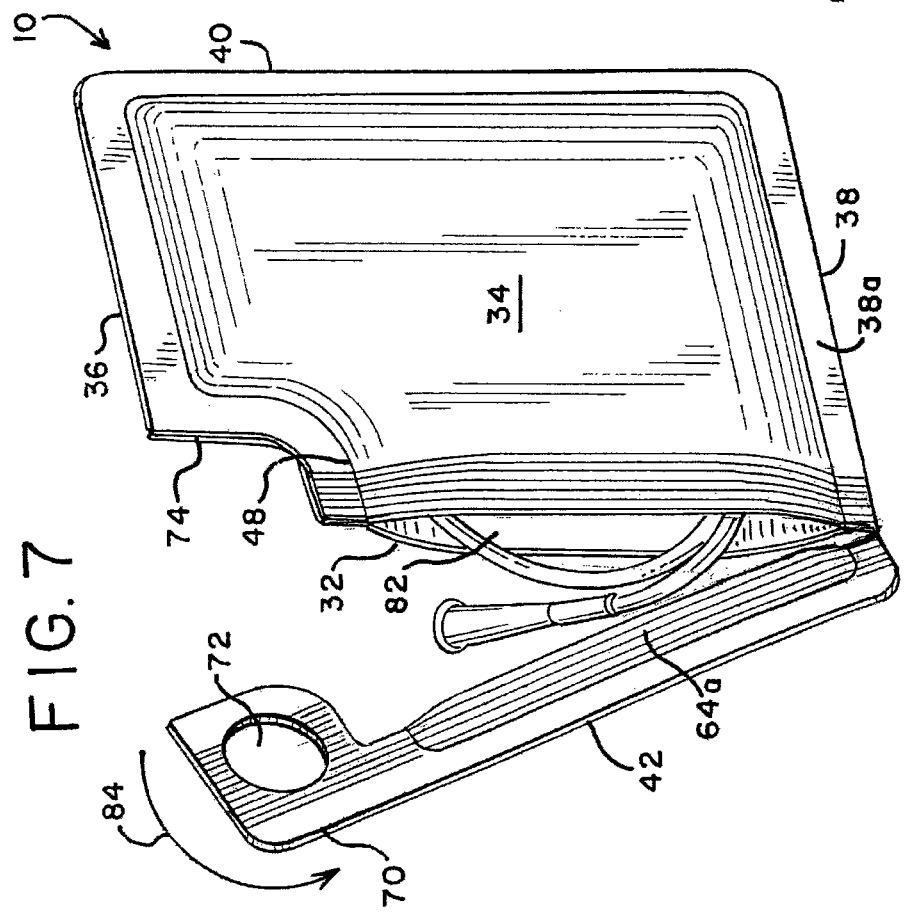

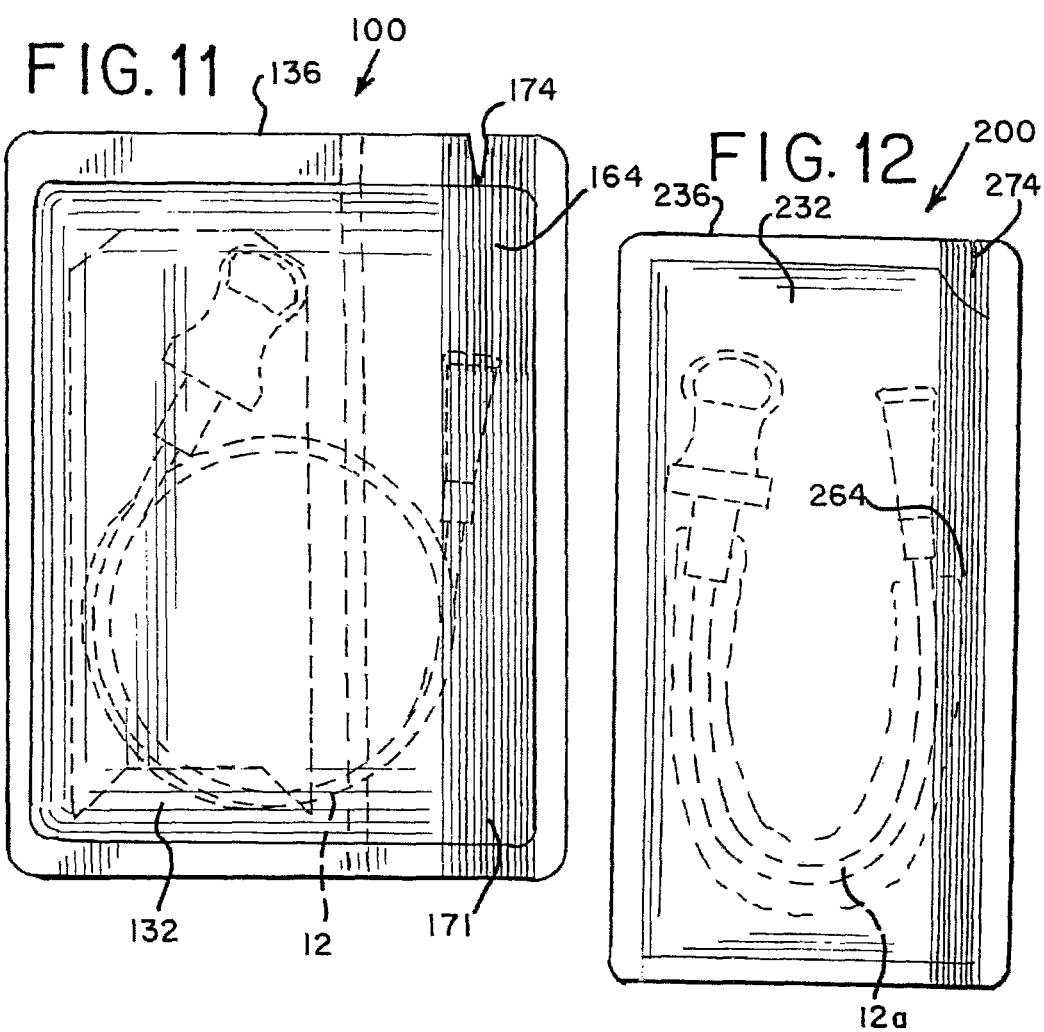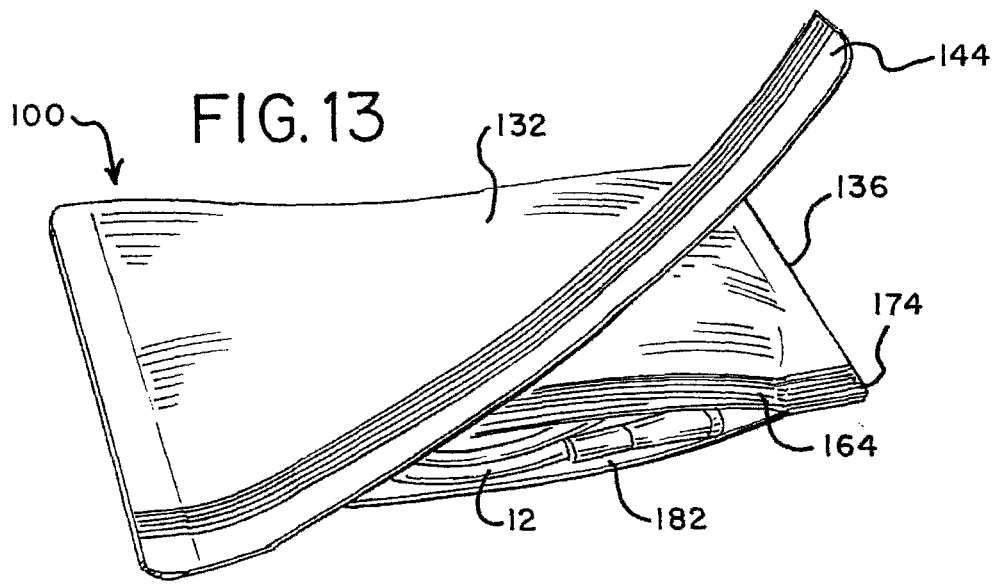

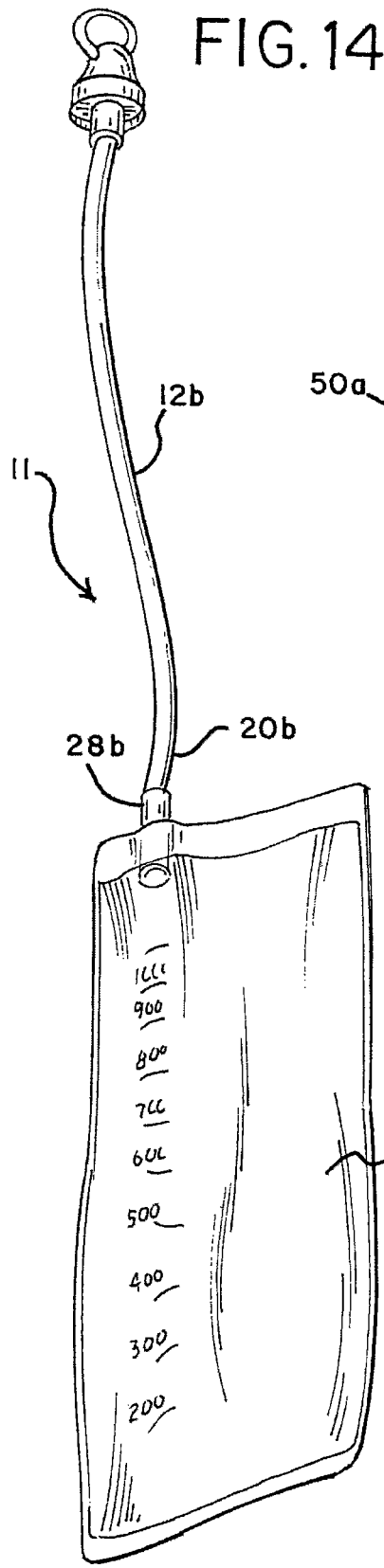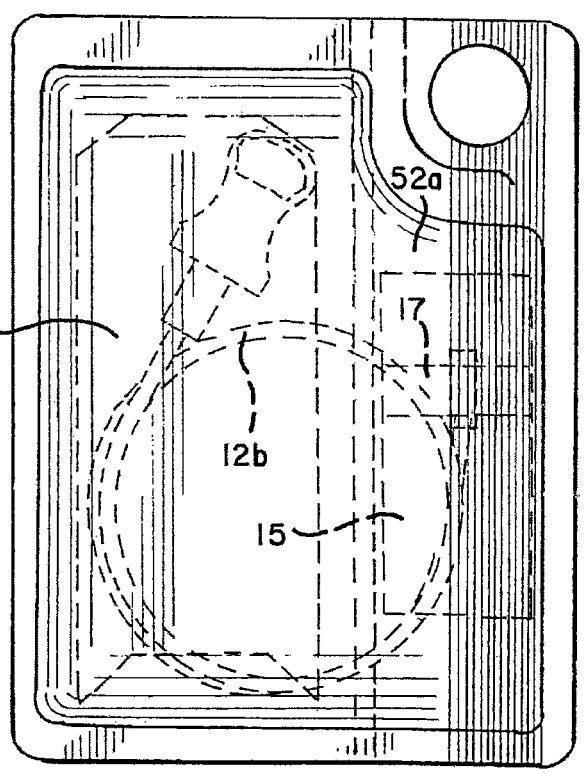

MEDICAL PRODUCT PACKAGE

The present application is the U.S. National Stage of PCT International Patent Application No. PCT/US2013/031480, filed Mar. 14, 2013, which is hereby incorporated herein by reference.

FIELD OF THE DISCLOSURE

The present disclosure is generally related to compact medical product packaging and, more particularly, to compact urinary catheter packaging.

BACKGROUND

Catheters are used to treat many different types of medical conditions and typically include an elongated catheter tube that is inserted into and through a passageway or lumen of the body. Urinary catheters, and in particular intermittent urinary catheters, are a good option for those who suffer from various abnormalities of the urinary system, such as urinary incontinence. With the advent of intermittent urinary catheters, individuals with urinary system abnormalities can conveniently self-catheterize to drain the individual's bladder.

Individuals who use intermittent urinary catheters typically use several single-use, individually packaged, sterile ready-to-use catheters every day. Oftentimes, such use occurs outside the home and in public restrooms. When outside of the home, intermittent catheter users must carry a supply of the single-use, ready-to-use catheters. Existing catheters, particularly for male users, have considerable length, which is typically between 30 cm (12 inches) and 40 cm (16 inches). Many commercially available single-use catheters are packaged in an elongated condition wherein the catheter package containing the catheter is relatively narrow and long. Such packages extend beyond the length of the catheter and can be up to about 48 cm (19 inches) in length.

A desired criterion for single-use, ready-to-use catheters is that the packaging be user-friendly. Carrying and transporting such elongated packages while outside of the home may be awkward and may make the user uncomfortable, especially for those who desire to be discreet. Additionally, users that have trouble with dexterity may find it difficult to handle and open such elongated packages. Therefore, the existing catheter packaging may not be ideal for some users in that such packaging may be difficult to store and carry, more conspicuous than some users would prefer, and hard to handle and open for those who have trouble with dexterity.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a catheter and package combination including a generally rectangular package having opposed front and rear panels that are sealed together to define a sealed interior cavity. The package has top and bottom edges and opposed side edges. The cavity has a first height extending in a direction between the top and bottom edges. The front and rear panels are configured to tear adjacent to one of the side edges in the direction between the top and bottom edges to form an opening in communication with the cavity. The opening has a second height in the direction between the top and bottom edges that is smaller than the first height of the cavity. A urinary catheter in a compact configuration is disposed within the cavity.

In another aspect, a catheter and package combination includes a package having opposed front and rear panels that are sealed together to define a sealed interior cavity. The package has top and bottom edges and opposed side edges. The cavity includes a first portion that has a first height extending in a direction between the top and the bottom edges, and the cavity includes a second portion that has a second height extending in the direction between the top and bottom edge wherein the second height is shorter than the first height. The front and rear panels are configured to tear in the direction between the top and bottom edges to form an opening in communication with the second portion of the cavity. A urinary catheter in a compact configuration is disposed within the cavity.

In a further aspect, a catheter and package combination includes a package having opposed front and rear panels that are sealed together to define a sealed interior cavity. The package has top and bottom edges and opposed side edges. The cavity includes a first portion that has a first height extending in a direction between the top and the bottom edges, and the cavity includes a second portion that has a second height extending in the direction between the top and bottom edges wherein the second height is shorter than the first height. A catheter in a coiled configuration is disposed within the cavity wherein the catheter has a hydrophilic surface. An amount of liquid is disposed within the cavity for hydrating the hydrophilic surface of the catheter. The front and rear panels include a directional tear element that propagates tearing of the panels along a desired line in the direction between the top and bottom edges to form an opening in communication with the second portion of the cavity. The opening has a third height in the direction between the top and bottom edges wherein the third height is shorter than the first height. The package also includes a tear initiation element for initiating tearing of the front and back panels.

BRIEF DESCRIPTION OF THE DRAWINGS

FIG. 1 is a front perspective view of one embodiment of a medical product package of the present disclosure;

FIG. 2 is a rear perspective view of the package of FIG. 1;

FIG. 3 is a front elevational view of the package of FIG. 1 shown with a catheter in a compact configuration within the package;

FIG. 4 is a plan view of the catheter of FIG. 3 shown in an elongated configuration;

FIG. 5 is a cross-sectional view of the package of FIG. 3 taken along lines 5-5;

FIG. 6 is a front perspective view of the package of FIG. 1 shown in an open configuration;

FIG. 7 is a rear perspective view of the package of FIG. 1 shown in an open configuration;

FIGS. 8-10 are cross-sectional views of alternative embodiments of the medical package of the present disclosure;

FIG. 11 is a front elevational view of another embodiment of a medical package of the present disclosure;

FIG. 12 is a front elevational view of another embodiment of a medical package of the present disclosure;

FIG. 13 is a perspective view of the packaging of FIG. 11 shown in an opened configuration;

FIG. 14 is a perspective view of another embodiment of a catheter assembly of the present disclosure;

FIG. 15 is a front elevational view of the package of FIG. 1 shown with the catheter assembly of FIG. 14 in a compact configuration within the package;

DESCRIPTION OF THE ILLUSTRATED EMBODIMENTS

Figure 16:
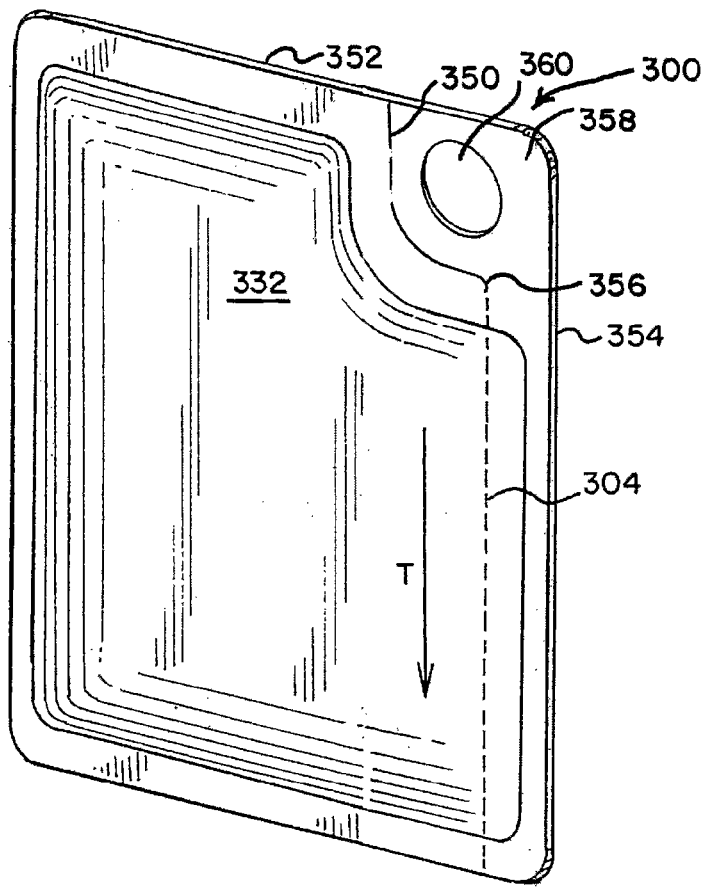
FIG. 16 is a front perspective view of another embodiment of a medical product package of the present disclosure.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

FIGS. 1-3 illustrate one embodiment of a package 10 for containing a medical product. Package 10 is described herein as packaging for a urinary catheter; however, package 10 also may be used as packaging for other medical products as well. Package 10 is particularly useful in compact packaging of elongated medical products that can be coiled, folded, curved or bent into a compact configuration for placement within the package 10.

Package 10 is preferably liquid and gas impermeable and may be made from any suitable liquid and gas impermeable materials, such as foils, polymers or multilayer films or laminates containing layers of metallic and/or polymer materials. In one embodiment, the package is made from aluminum foil. In another embodiment, the package is made from a polymer film. In yet another embodiment the package is made from a multilayered film including a polymer overlaying a foil, such as polypropylene covered aluminum foil. When the package is made entirely of polymers or a polymer covered foil, the polymer may be, for example, one or more of polypropylene, polyethylene, polyamide, polyester, polyurethane, ethylene-vinyl acetate, polychlorotrifluoroethylene and co-polymers thereof. As explained in more detail with respect to FIGS. 16-21 such polymers may be oriented (aligned) polymers. The oriented polymers may include, for example, monoaxially oriented polypropylene (MOPP) or biaxially oriented polypropylene (BOPP), oriented polyamide (OPA), monoaxially or biaxially oriented polyester, monoaxially or biaxially oriented polyurethane, monoaxially or biaxially oriented ethylene-vinyl acetate, and monoaxially or biaxially oriented polychlorotrifluoroethylene. In one example, package 10 is made from a Surlyn® resin coated foil supplied by Du Pont. In one embodiment, the package 10 is made of a multilayered film including layers of polypropylene, polyethylene, aluminum foil and Surlyn. The film may include, for example, a 25.4 µ outer layer of oriented polypropylene, 25.4 µ intermediate layer of low density polyethylene, 8.9 µ intermediate layer of aluminum foil and 44.4 µ inner layer of Surlyn®.

One benefit of the use of a Surlyn® in the multilayered film is that the Surlyn® resin reduces the noise or crinkle of the package when the package is manipulated and handled by the end user during opening of the package and removal of its contents. Such noise or crinkle reduction may be desired by user's that desire discreetness when using the medical product, such as a catheter, in public places.

In the embodiment illustrated in FIGS. 1-3, package 10 is generally rectangular and may be sized or configured to fit easily within a standard shirt front pocket or within a standard pants back pocket. The standard front pocket of a dress shirt has a width of about 100 mm and a height of about 130 mm and the standard back pocket of a pair of pants has a height of about 140 mm and a width of about 120 mm. Front shirt pockets and back pants pockets may vary and when package 10 has larger dimensions than that of the shirt or pants pocket, the package may wrinkle or bend to fit within the pocket or may stick slightly out of the opening of the pocket. The package also may be shapes other than rectangle. For example, the package 10 may be generally round (e.g. circular, oval, ellipse, etc.) or generally square.

Referring to FIG. 3, the height H of package 10 may be between about 120 mm and about 160 mm and is preferably about 140 mm as measured from top edge 36 to bottom edge 38. The width W of package 10 may be between about 75 mm and about 120 mm and is preferably about 110 mm as measured from side edge 40 to side edge 42. The height to length ratio of package 10 may be between about 1.3 to about 2.1 and is preferably about 1.3. The height and width of package 10 may also be larger or smaller than the above-mentioned dimensions depending on the intended use.

The package 10 includes an elongated medical product, such as a urinary catheter 12, disposed in a compact configuration within a cavity 14 (FIGS. 3 and 5) of package 10. In the compact configuration, catheter 12 may be coiled, folded, curved and/or bent. In FIG. 3, elongated catheter tube 12 is shown in a curved compact configuration and, in particular, in a wound or coiled compact configuration. The catheter 12 may be any suitable urinary catheter used for bladder drainage. FIG. 4 illustrates catheter 12 in an elongated configuration. In the illustrated embodiment, catheter 12 includes an elongated catheter tube 16 having a proximal insertion end portion 18 and a distal end portion 20.

Catheter 12 also includes one or more drainage eyes or openings 22 at or near the proximal insertion end 18 of the catheter tube 16 for draining the bladder. Catheter 12, optionally, may include a soft, typically rubbery introducer tip 24 adjacent proximal end 18 and may, optionally, include an end cap 26 that covers and protects the introducer tip 24. A connector or drainage member 28, which may be a funnel, is located at the distal end 20 of the catheter tube 16.

As explained in more detail below, package 10 may be configured for liquid or vapor hydration of a hydrophilic coated catheter disposed within package 10. In such an embodiment, catheter tube 16 includes an outer surface having a hydrophilic coating on at least a portion thereof. The details of such hydrophilic catheters are described in U.S. Pat. No. 8,051,981, which is hereby incorporated herein by reference. The hydrophilic coating of the catheter tube 16 is wetted, hydrated or otherwise activated within the package 10 to result in a highly lubricious condition that eases insertion of catheter 12 into and through the urethra.

Catheter 12, optionally, also may include a thin flexible sleeve 30 that covers the outer surface of the catheter tube 16. Sleeve 30 may be formed of any variety of thin flexible polymeric film materials, such as polyethylene, plasticized PVC, polypropylene, polyurethane or elastomeric hydrogels. The user may handle and manipulate catheter tube 16 through sleeve 30 which provides a contamination barrier between the user's hands and catheter tube 16. For example, when catheter 12 is being inserted into the urethra, the user grasps and handles catheter tube 16 through the sleeve 30. When catheter tube 16 includes a hydrophilic coating thereon, the sleeve 30 may be liquid and/or vapor permeable so as to allow liquid and/or vapor therethrough to hydrate the hydrophilic coating while catheter 12 is stored within package 10. When package 10 is configured for vapor hydration, sleeve 30 is preferably liquid impermeable and vapor permeable.

FIG. 1 shows a front view of package 10 while FIG. 2 shows a rear view. Package 10 includes a front panel 32 (FIG. 1) and a rear panel 34 (FIG. 2), which may be mirror images of each other. Front panel 32 and rear panel 34 are affixed or peripherally sealed to each other along their edges to define inner cavity 14 (FIG. 5) for containing a medical product, such as catheter 12 in a compact configuration. Preferably, front panel 32 and rear panel 34 are two separate sheets of material in which the confronting edges of front and rear panels 32, 34 are peripherally sealed to form top edge 36, bottom edge 38, opposing side edges 40, 42 and a corner seal 44. The edges of the front and rear panels 32, 34 may be sealed by any suitable sealing method which may include, for example, heat and/or adhesive sealing. In the illustrated embodiment, top edge 36 of package 10 is formed by seal 36a, bottom edge 38 is formed by seal 38a, side edge 40 is formed by seal 40a, and side edge 42 is formed by seal 42a. The peripheral seal along the edges of package 10 at least substantially forms or defines sealed cavity 14. In the illustrated embodiment, a portion of cavity 14 may be defined by corner seal 44. Corner seal 44 has a generally rectangular or square shape and includes two sections, a first seal section 46 that extends generally vertically downward from top edge 36 and a second seal section 48 that extends generally horizontally inward from side edge 42.

In an alternative embodiment, front panel 32 and rear panel 34 may be part of a single sheet (which may be a multilayered film) that is folded so as to define the front and rear panels 32, 34, where the folded section of the sheet defines one of the edges. For example, bottom edge 38 shown in FIGS. 1 and 2 may be a fold of the sheet instead of a seal between two separate sheets.

Referring to FIG. 1, in the illustrated embodiment, cavity 14 includes a first portion 50 that has a height X that is greater than a height Y of a second portion 52. Both heights X and Y are measured in a direction between top edge 36 and bottom edge 38 and that is parallel to side edges 40, 42. As used herein "measured in a direction between top edge 36 and bottom edge 38" means the height extends in such direction and does not necessary extend all the way to the top and/or bottom edges. In the illustrated embodiment, the boundary of first portion 50 is at least partially defined by top seal 36a, side seal 40a and the first corner seal section 46. As shown in FIG. 1, height X of portion 50 extends between top sealed 36a and bottom seal 38a. The boundary of portion 52 is at least partially defined by the second corner seal section 48, bottom seal 38a and side seal 42a. Height of portion 52 extends between bottom seal 38a and the generally horizontally extending second seal section 48 of corner seal 44. As illustrated in FIG. 3, the majority of catheter 12 in the compact coiled configuration resides in first portion 50 of cavity 14. In other embodiments heights X and Y may extend all the way to top and bottom edges 36, 38.

When catheter 12 is a hydrophilic catheter, package 10 may include one or more sources for hydrating the hydrophilic surface of the catheter while the catheter is stored within the package. For example, an amount of liquid for contacting and hydrating the hydrophilic surface of the catheter 12 may be contained (or provided) within cavity 14 of package 10. In an alternative embodiment, an amount of vapor donating liquid that provides a vapor for vapor hydrating the hydrophilic surface of the catheter 12 may be disposed within cavity 14.

Referring to FIGS. 3 and 5, when package 10 is configured for vapor hydration of a hydrophilic catheter, the package 10 may include a wicking element 54 (best shown in FIG. 5, shown in phantom in FIG. 3) that is disposed on an inner surface 56 of the rear panel 34. Wicking element 54 also may be disposed on the inner surface of front panel 32. Wicking element 54 may be attached to inner surface 56 by, for example, an adhesive. Alternatively, wicking element 54 may be loosely placed (i.e., not physically attached) within cavity 14 such as against inner surface 56. The wicking element 54 may comprise any suitable wicking material, such as, for example, a fabric, absorbent or an absorbent open cell foam and may be in the form of a strip of such material. The wicking element 54 is wetted with a vapor donating liquid, such as pure water or an aqueous solution, preferably at a point in time prior to when the sealed cavity 14 is formed.

Package 10 also includes a gas permeable, liquid impermeable barrier 58 (best shown in FIG. 5, shown in phantom in FIG. 3) that covers the inner surface 56 of the panel (34 or 32) against which wicking element 54 is disposed. The edges 55 of barrier 58 may be, for example, heat sealed to inner surface 56 of rear panel 34 after wicking element 54 has been wetted with a vapor donating liquid medium. A portion of edge 55 of barrier 58 may be sealed to inner surface 56 of the rear panel 34 by being positioned between the edges of front panel 32 and rear panel 34 and being sealed by seals 36a, 38a and 40a. As illustrated in FIG. 5, edge 55 of barrier 58 is positioned between and captured by confronting edges of front panel 32 and bottom panel 34 and sealed by seal 40a.

Referring to FIG. 5, barrier 58 separates sealed cavity 14 into a first compartment 60 containing the catheter 12 and a second compartment 62 containing the liquid wet wicking element 54 such that the catheter 12 is not in direct contact with the vapor donating liquid contained within second compartment 62. The wicking element 54 provides for at least substantially uniform distribution of liquid in compartment 62. As noted above, the vapor donating liquid is preferably pure water or an aqueous solution that produces a vapor, preferably water vapor, which results in a vapor atmosphere within the sealed cavity 14. When the vapor is a water vapor, the vapor results in a vapor atmosphere of between 90%-100% relative humidity within cavity 14 and more preferably 100% relative humidity. The vapor is absorbed by the hydrophilic coating on the catheter 12 to hydrate or activate the hydrophilic coating.

Packages of the type described herein include an opening element that is easy to use particularly, by individuals of limited or unequal dexterity. Turning to FIGS. 1-3, front panel 32 includes a first directional tear element, such as tear tape 64, and rear panel 34 includes a second directional tear element, such as tear tape 64a. Tear tape 64 overlays outer surface 66 of the front panel 32 and tear tape 64a overlays outer surface 68 of rear panel 34, and each of tear tape 64, 64a extend in a direction between top edge 36 and bottom edge 38. The directional tear tape 64, 64a may be applied to outer surface 66 of front panel 32 and outer surface 68 of rear panel 34, respectively at or adjacent to edge 42. The tear tape 64, 64a may be applied before or after the package 10 has been sealed with catheter 12 disposed therein. Tear tape 64, 64a includes a plurality of substantially straight, vertically extending alternating ridges 69 and grooves 71. The tear tape 64, 64a and the ridges 69 thereon may extend from top edge 36 to bottom edge 38. In an alternative embodiment tear tape 64, 64a and/or the ridges 69 of the tear tape may only partly extend between top edge 36 and bottom edge 38. As will be discussed in further detail below, the tear tape 64, 64a result in package opening that preferably forms a generally straight vertically extending opening. Preferably the opening is made along an intended line.

Package 10 may include a tab 70 that can be gripped and pulled to form an opening within package 10 or commence the opening sequence. Tab 70, optionally, may include a gripping element, such as the illustrated pull ring or finger hole 72, for ease of gripping and pulling tab 70. Finger hole 72 extends through front panel 32 and rear panel 34 and may be formed by punching or otherwise cutting out material from front panel 32 and rear panel 34. Preferably, finger hole or pull ring 72 is formed after package 10 has been sealed and tear tape 64 has been applied. In an alternative embodiment, tab 70 is solid and does not include a finger hole.

Package 10 also includes a tear line 74 that at least partially defines tab 70. The tear line 74 extends downwardly from top edge 36 of package 10 and curves in a direction toward side edge 42. When tab 70 includes finger hole 72, the tear line may curve at least partially around the finger hole. In any event, the tear line 74 extends to or near tear tape 64, 64a. Tear line 74 may include a downward projecting segment 76 that extends substantially vertically within the region of tear tape 64, 64a and in the direction of the grooves or ridges of tape 64, 64a. Tear line 74 may be a score line or cut line that extends through front panel 32 and rear panel 34. When tear line 74 is a cut line that extends through front and rear panels 32, 34, the cut line may be broken up into discrete segments separated by intervening attached portions or notches 78 that keep tab 72 attached to the package until use.

Turning to FIG. 6, to open package 10, a user may grip tab 70 by finger hole 72, when one is present, and pull tab 70 forward or backward away from the rest of the package and in a downward direction. In FIG. 6, with the front panel 32 facing the user, tab 70 is pulled backward and downward and away from the user, as shown by arrow 80. As the user pulls tab 70, the package 10 tears along tear line 74 and tear line 74 propagates or advances the tear toward directional tear tape 64, 64a. As the package tears in the region of directional tear tape 64, 64a, the tear tape causes front and rear panels 32, 34 to tear along a desired line, which in the illustrated embodiment is a substantially straight vertical line. In particular, once the tear starts down one of the grooves 71 located between the ridges 69, the tape advances the tear along that particular groove. Tearing of front and rear panels 32, 34 results in a substantially straight, clean and uniform vertical opening 82 that extends from bottom seal 38a to corner seal section 48. The opening has a height Z, as measured in a direction between top edge 36 and bottom edge 38 and that is generally parallel with side edge 40, height 2 is smaller than height X of first portion 50. The opening being smaller than first portion 50 is beneficial in that the smaller opening tends to keep catheter 12 from inadvertently falling out of package 10 upon opening of the package. In this embodiment, the compact coiled configuration of catheter 12 has a natural tendency toward uncoiling and expanding radially outwardly. As such, the coil tends to expand within and substantially occupy first portion 50. As the second portion 52 and/or opening 82 are smaller than the first portion 50, the catheter is more likely to remain in cavity 14 upon opening. Once the opening 82 is created, the user grips and pulls the catheter out of the package 10 for use.

As illustrated in FIG. 7, because the front and rear panels 32, 34 are mirror images of each other and both have tear tape 64, 64a in approximately the same location, the package 10 may be just as easily opened with rear panel 34 facing the user. The user pulls the tab 70 downward and backward from the user, as indicated by arrow 84. As discussed above, oftentimes users of urinary catheters have trouble with dexterity and may have more control of one hand over the other. While most likely unintentional, some of the commercially available ready-to-use catheters are packaged in packaging that tends to be easier to open for either a right handed or left handed individual. In such instances, it will be harder for one group of users to open the package unless the manufacture makes two different package configurations, e.g., one for right hand dominant individuals and one for left hand dominant individuals. In general, it is usually more expensive for manufactures to make two different package configurations and thus most manufactures opt to make one package. As can be seen by FIGS. 6 and 7, one of the benefits of package 10 is that the package is equally openable by both right and left handed individuals. As such package 20 serves most users and avoids the cost of manufacturing different package configurations, based on the dexterity or the right/left handedness of the users.

FIGS. 8-10 illustrate alternate embodiments of vapor hydrating a hydrophilic catheter within package 10. Many of the features of these embodiments are substantially similar to those of the previous embodiment and thus carry identical reference numerals for identical elements. Turning first to FIG. 8, package 10 includes a wicking element 54 that is disposed within cavity 14. The wicking element 54 may be affixed to inner surface 56 of rear panel 34 or may be loosely placed within cavity 14. The wicking element 54 is wetted with a vapor donating liquid that provides a vapor which hydrates the hydrophilic surface on catheter 12 while the catheter is stored therein.

In FIG. 9, package 10 includes a gas permeable, liquid impermeable barrier 58 but without wicking element 54. The edges of barrier 58 are sealed to the inner surface 56 of rear panel 34 to form a sealed compartment 87 which contains a vapor donating liquid 86. The vapor donating liquid 86 provides a vapor that permeates through barrier 56 and contacts the hydrophilic surface of catheter 12 to wet the surface while catheter 12 is disposed and stored within cavity 14.

In FIG. 10, package 10 includes one or more sachets 88 disposed in cavity 14. Sachet 88 may be attached to inner surface 56 of the rear panel 34 or may be loosely placed within package 10. Sachet 88 may be at least partially made from a vapor permeable, liquid impermeable material and defines a sealed compartment 90 within cavity 14. In the illustrated embodiment, a wicking element 54 is disposed within the sealed compartment 90 of sachet 88. The wicking element 54 is wetted with a vapor donating liquid to provide a vapor that permeates through sachet 88 and contacts the hydrophilic surface of catheter 12 to wet the surface. In an alternative embodiment, wicking element 54 may be eliminated from sachet 88 and sachet 88 may only contain a vapor donating liquid in compartment 90.

FIG. 11 illustrates another embodiment of a package 100 of the present disclosure. Package 100 includes a front panel 132 and a rear panel (not shown) that are sealed together to form a sealed cavity that contains urinary catheter 12 in a compact configuration. In this embodiment, the cavity is generally uniform throughout. When the package 100 is configured for hydrating a hydrophilic catheter within the package, package 100 and the cavity formed therein may include any of the liquid or vapor hydrating configurations described above and/or shown in FIGS. 5 and 8-10.

As with the previously described package 10, package 100 includes a direction tear element, such as a strip of directional tear tape 164 vertically extending over front panel 132 and rear panel. Package 100 also includes a tear initiation element 174, such as a tear line, notch or slit, extending from top edge 136 to at or near the tear tape 164. The tear initiation element 174 extends through the front and rear panels and initiates tearing of the package.

Package 200 shown in FIG. 12 is similar to that of FIG. 11 except that the package is narrower and it includes a shorter length catheter 12a disposed within a sealed cavity of the package. Catheter 12a may have the same features as catheter 12 disclosed above except that it is much shorter in length because it is designed to be used by females (who have a much shorter urethra than males). In this embodiment, catheter 12a has a compact bent, curved or arcuate configuration when placed within cavity 14. When package 200 is configured for hydration of a hydrophilic catheter, package 200 and the cavity formed therein may include any of the liquid or vapor hydrating configurations described above and/or shown in FIGS. 5 and 8-10. Similar to package 100, package 200 includes tear tape 264 extending over a portion of each of the front panel 232 and rear panel (not shown). Package 200 also includes a tear initiation element 274, such as a tear line, notch or slit that extends from top edge 236 to at or near tear tape 264.

Packages 100 and 200 may be opened in similar fashion and such opening is now described in relation to package 100. Referring to FIG. 13, package 100 may be opened by gripping corner 144 of the package and pulling the corner downward and away from the package 100. The tear initiation element 174 propagates or advances the tear in or toward the tear tape 164 and into one of the grooves 171 (FIG. 11) of the tear tape 164. As the user pulls the corner 144, the package 100 tears down the one of the grooves 171 and in a substantially straight line to form a substantially straight opening 182.

FIGS. 14 and 15 illustrate another embodiment of a catheter package of the present disclosure. As illustrated in FIG. 14, the catheter assembly 11 includes catheter 12b having similar features to catheter 12 described above. In this embodiment, catheter 12b includes a connection member 28b at the distal end portion 20b thereof that is attached to a collection bag 15. Referring to FIG. 15, package 10a is substantially identical to the package shown in FIGS. 1-10. In the compact configuration, catheter 12b is coiled and collection bag 15 is in a folded configuration. A restraining member 17, such as a band and preferably a paper band, retains the collection bag 15 in the folded configuration. As illustrated, the catheter 12b in the coiled compact configuration substantially resides in portion 50a while collection bag resides in the second portion 52a of cavity 14.

FIG. 16 illustrates another embodiment of a package 300 of the present disclosure. Package 300 is substantially similar to that of package 10 except that the directional tear element comprises an oriented polymer film in which high linear molecular orientation in one direction is provided and molecular orientation in another direction perpendicular to the one direction is extremely low. The higher side molecular orientation is directed in parallel and coincides with a desired tearing direction. In the illustrated embodiment, package 300 includes a front panel 332 and a rear panel (not shown). The front panel 332 and rear panel are made from a film that includes an oriented polymer wherein the high linear molecular orientation of the polymer is in parallel with tearing direction T for facilitating tearing of the front panel 332 and rear panel (not shown) in the tearing direction along line 304 (shown in phantom) of package 300.

The oriented polymers may include monoaxial and biaxial oriented polymers. Such polymers may include, for example, MOPP, BOPP, OPA, monoaxially or biaxially oriented polyester, monoaxially or biaxially oriented polyurethane, monoaxially or biaxially oriented ethylene-vinyl acetate, and monoaxially or biaxially oriented polychlorotrifluoroethylene.

Figure 17:
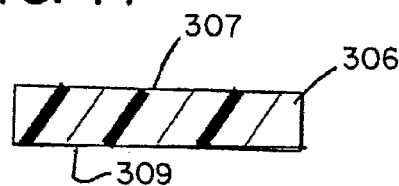
FIGS. 17-21 are cross-sectional views of films that may be used to form a medical product package in accordance with the present disclosure.

FIGS. 17-21 illustrate different films from which package 300 may be made. Referring to FIG. 17, packaging film 306 may include a single layer of a liquid and gas impermeable oriented polymer having directional tear properties wherein surface 307 of film 306 serves as the outer surface of the package, as surface 309 servers as the inner surface of the package.

Figure 18:
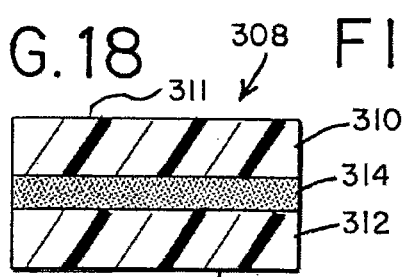

Turning to FIG. 18, a multilayered packaging film 308 has three layers including a first layer 310 of an oriented polymer which includes directional tear properties. The layer 310 has an outer surface 311 that will serve as the outer surface of the package. A second adhesive layer 314 is interposed between first layer 310 and a third layer 312 wherein the adhesive layer 314 bonds the first and third layers 310, 312. The third layer 312 is a polymer layer and has a surface 313 that serves as the inner surface of the package. At least one of the polymers of the first and second layers 310, 312 is comprised of a liquid and gas impermeable polymer.

Figure 19:
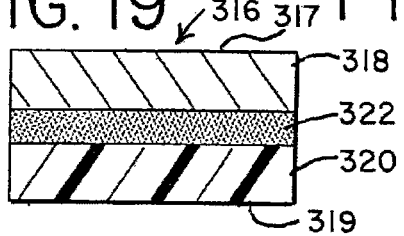

FIG. 19 illustrates an alternative embodiment of a multilayered packaging film 316 which as three layers including an outer foil layer 318 which has an outer surface 317 that will serve as the outer surface of the package. Foil layer 318 may be, for example, a layer of aluminum foil. A second adhesive layer 322 is interposed between the first layer 318 and a third layer 320 of an oriented polymer having directional tear properties. The second adhesive layer 322 bonds the first and third layers 318, 320. Third layer 320 has a surface 319 which will serve as the inner surface of the package.

Figure 20:
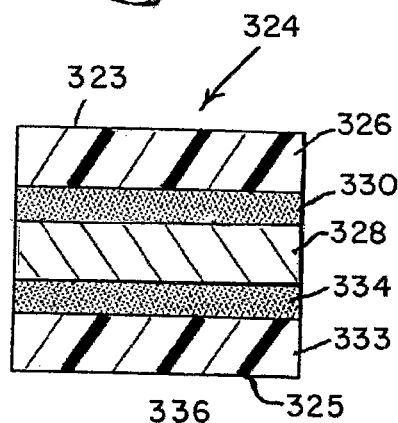

In the embodiment illustrated in FIG. 20, a multilayer packaging film 324 has five layers including a first layer 326 of oriented polymer which has directional tear properties. The first layer 326 has an outer surface 323 that will serve as the outer layer of the package. A second layer 330 of adhesive is interposed between first layer 326 and a third layer 328 of foil. A forth layer 334 comprising an adhesive is interposed between the third layer 328 and a fifth layer 333 which is comprised of a polymer. The polymer of the fifth layer 333 may be an oriented or a non-aligned polymer. Surface 325 of fifth layer 333 will serve as the inner surface of the package.

Figure 21:
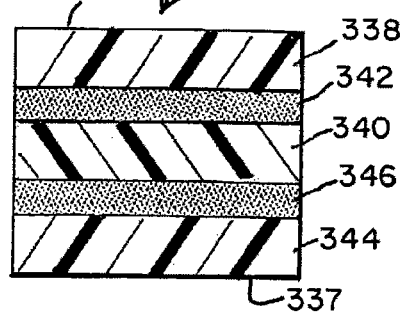

In the embodiment illustrated in FIG. 21, the multilayer film 336 has five layers including a first layer 338 of an oriented polymer having directional tear properties wherein the outer surface 335 of first layer 338 will serve as the outer surface of the package. A second layer 342 of adhesive is interposed between the first layer 338 and a third layer 340 comprising a polymer wherein the polymer of the third layer 340 is a non-aligned polymer. The film 336 also includes a fourth layer 346 comprising an adhesive interposed between the third layer 340 and a fifth layer 344 comprising a polymer that may be an oriented or a non-aligned polymer.

The fifth layer 344 includes a surface 337 that will serve as the inner surface of the package.

Referring back to FIG. 16, the high linear molecular orientations of the oriented polymer layers of the packing films that form the front and rear panels of package 300 are in parallel with tear direction T. Package 300 also includes a tear initiation element, such as tear line 350, that extends from top edge 352 toward side edge 354. The tear line 350 has a downward extending portion 356 that extends in the same direction as the high linear molecular orientations of the packaging film. To open the package, the user grips tab 358, preferably by finger hole 360, when one is present, and pulls downward in a direction to tear the package along tear line 350. Tear line 350 propagates the tear in a direction parallel to the linear molecular orientation of the oriented polymer of the front and rear panels, which panels tear along line 304 (shown in phantom). Tearing along the linear molecular orientation of the polymer results in a substantially straight and clean tear which results in a substantially straight vertically extending opening.

It will be understood that FIG. 16 provides an example of one package made from the above discussed oriented polymer films and that such films may be used in the construction of any of the packages described herein including, without limitation the packages described above and shown in FIGS. 1-10, 11, and 15.

In other embodiments, the directional tear element may be a vertical score in front and rear panels formed, for example, by laser scoring.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims.

The invention claimed is:

1. A catheter and package combination, comprising:
   a generally rectangular package having opposed front and rear panels that are sealed together to define a sealed interior cavity, the package having top and bottom edges and opposed side edges;
   the cavity having a first height extending in a direction between the top and bottom edges;
   the front and rear panels being configured to tear adjacent to one of the side edges in the direction between the top and bottom edges to form an opening in communication with the cavity, the opening having a second height in the direction between the top and bottom edges that is smaller than the first height of the cavity; and
   a urinary catheter in a compact configuration disposed within the cavity wherein the compact configuration of the catheter has a dimension in the direction between the top and bottom edges of the package and the height of the opening being smaller than said dimension of the compact configuration of the catheter.

2. The catheter and package combination of claim 1 wherein the front and rear panels tear in a desired line.

3. The catheter and package combination of claim 2 wherein the desired line is substantially straight.

4. The catheter and package combination of claim 1 further including a directional tear element associated with the front and rear panels for propagating the tearing of front and rear panels.

5. The catheter and package combination of claim 4 wherein the directional tear element comprises a first tear tape overlying an exterior surface of the front panel and a second tear tape overlying an exterior surface of the rear panel.

6. The catheter and package combination of claim 4 wherein the directional tear element comprises an oriented polymer.

7. The catheter and package combination of claim 4 further including a tear initiation element.

8. The catheter and package combination of claim 7 wherein the tear initiation element comprises a tear-line, precut-line, notch, slit, or score-line.

9. The catheter and package combination of claim 7 wherein the tear initiation element extends from the top edge to at or near the directional tear element.

10. The catheter and package combination of claim 1 wherein the package is formed from a foil.

11. The catheter and package combination of claim 1 wherein the package is formed from a multilayered packaging film.

12. The catheter and package combination of claim 1 wherein the catheter includes a hydrophilic coating.

13. The catheter and package combination of claim 12 wherein an amount of liquid is disposed in the sealed cavity for hydrating the hydrophilic coating of the catheter and the liquid contacts the hydrophilic coating of the catheter to hydrate the hydrophilic coating.

14. The catheter and package combination of claim 1 wherein the catheter is in a coiled, curved, folded and/or bent configuration.

15. The catheter and package combination of claim 1 wherein the cavity includes a first portion having the first height and a second portion having a third height in the direction between the top and bottom edges wherein the third height is shorter than the first height.

16. The catheter and package combination of claim 15 wherein the catheter in the compact configuration resides substantially in the first portion of the cavity.

17. The catheter and package combination of claim 1 wherein the package is sized to fit in a standard front shirt pocket and/or a standard rear pants pocket.

18. The catheter and package combination of claim 1 wherein the package has a height between about 120 mm and about 160 mm and a width between about 75 mm and about 120 mm.

19. The catheter and package combination of claim 1 further including a collection bag attached to the urinary catheter.

20. A catheter and package combination, comprising:
   a generally rectangular package having front and rear panels and defining a sealed interior cavity, the package having top and bottom edges and opposed side edges;
   the cavity having a first height extending in a direction between the top and bottom edges;
   a catheter in a coiled configuration disposed within the cavity; and
   the front and rear panels being configured to tear adjacent to one of the side edges in the direction between the top and bottom edges to form an opening in communication with the cavity, the opening having a second height in the direction between the top and bottom edges that is smaller than the first height of the cavity and smaller than the coiled configuration of the catheter.

* * * * *